(12) United States Patent
Donzier (10) Patent No.: US 9,719,904 B2
(45) Date of Patent: Aug. 1, 2017

(54) DENSITY AND VISCOSITY SENSOR AND MEASURING METHOD

(71) Applicant: Eric Donzier, Bercheres sur Vesgre (FR)

(72) Inventor: Eric Donzier, Bercheres sur Vesgre (FR)

(73) Assignee: OPENFIELD, Versailles (FR)

( * ) Notice: Subject to any disclaimer, the term of this patent is extended or adjusted under 35 U.S.C. 154(b) by 170 days.

(21) Appl. No.: 14/394,085

(22) PCT Filed: Apr. 12, 2013

(86) PCT No.: PCT/EP2013/057747
§ 371 (c)(1),
(2) Date: Oct. 11, 2014

(87) PCT Pub. No.: WO2013/153224
PCT Pub. Date: Oct. 17, 2013

(65) Prior Publication Data
US 2015/0075279 A1    Mar. 19, 2015

(30) Foreign Application Priority Data
Apr. 12, 2012 (EP) .................................... 12305433

(51) Int. Cl.
*G01N 9/00* (2006.01)
*G01N 11/16* (2006.01)
(Continued)

(52) U.S. Cl.
CPC ............. *G01N 9/002* (2013.01); *E21B 49/08* (2013.01); *G01N 11/16* (2013.01); *G01N 29/036* (2013.01);
(Continued)

(58) Field of Classification Search
CPC ...................................................... G01N 9/002
See application file for complete search history.

(56) References Cited

U.S. PATENT DOCUMENTS 5,323,638 A    6/1994  Langdon
6,389,891 B1   5/2002  D'Angelico
(Continued)

FOREIGN PATENT DOCUMENTS

EP    0282251 A2    9/1988
EP    1698880 A1    9/2006

OTHER PUBLICATIONS

PCT/EP2013/057747, International Search Report, May 10, 2013, European Patent Office, P.B. 5818 Patentlaan 2 NL-2280 HV Rijswijk.
(Continued)

*Primary Examiner* — Ryan Walsh
(74) *Attorney, Agent, or Firm* — The Jansson Firm; Pehr Jansson (57) ABSTRACT

A density and viscosity sensor for measuring density and viscosity of a fluid, comprises:
  a housing (4) defining a chamber (8) isolated from the fluid (3), the housing (4) comprising an area defining a membrane (9) separating the chamber (8) from the fluid (3);
  a resonating element (5) arranged to be immersed in the fluid (3) and mechanically coupled to the membrane (9); and
  an actuating/detecting element (6) coupled to the resonating element (5), the actuating/detecting element (6) being positioned within the chamber (8) and mechanically coupled to the membrane (9), the actuating/detecting element (6) comprising at least one piezoelectric element (10) comprising two sides (11, 12) substantially parallel to the membrane (9);
(Continued)

The membrane (9) has a thickness enabling transfer of mechanical vibration between the actuating/detecting element (6) and the resonating element (5).

One side (11) of the piezoelectric element (10) comprises a single conductive area (13).

Another side (12) of the piezoelectric element (10) comprises at least two conductive areas (14A, 14B, 14C, 14D, 14E, 14F, 14G, 14H) isolated from each other, each conductive area (14A, 14B, 14C, 14D, 14E, 14F, 14G, 14H) being coupled to an electrical potential (V1, V2) of opposite sign relatively to adjacent areas such that the resonating element (5) is driven to vibrate in a selected plane (P1, P2) perpendicular to the membrane (9).

23 Claims, 7 Drawing Sheets

(51) Int. Cl.
*G01N 29/036* (2006.01)
*E21B 49/08* (2006.01)

(52) U.S. Cl.
CPC ............ *G01N 2009/006* (2013.01); *G01N 2291/02818* (2013.01); *G01N 2291/2634* (2013.01)

(56) References Cited

U.S. PATENT DOCUMENTS

| | | | |
|---|---|---|---|
| 7,874,199 | B2 | 1/2011 | Chaudoreille et al. |
| 7,958,772 | B2 | 6/2011 | Permuy et al. |
| 2008/0034840 | A1* | 2/2008 | Mutharasan ......... G01N 29/022 73/24.01 |
| 2010/0154546 | A1 | 6/2010 | D'Angelico et al. |
| 2015/0300894 | A1* | 10/2015 | Robutel ............... G01N 29/036 310/323.21 |

OTHER PUBLICATIONS

PCT/EP2013/057747, Written Opinion of the International Searching Authority, May 10, 2013, European Patent Office, P.B. 5818 Patentlaan 2 NL-2280 HV Rijswijk.

\* cited by examiner

DENSITY AND VISCOSITY SENSOR AND MEASURING METHOD

BACKGROUND

1. Field of the Invention

An aspect of the invention relates to a density and viscosity sensor. The invention further relates to a density and viscosity measuring method.

Such a density and viscosity sensor and measuring method find a particular, though non exclusive, application in measuring density and viscosity of fluids in harsh environment including high pressure conditions, high or low temperature conditions, or a combination of both conditions. Such harsh environments may be found with respect to measurement applications in desert region, in arctic region, in deep sea zone, in subterranean zone, etc. . . .

2. Description of the Related Art

The document EP 1 698 880 describes a density and viscosity sensor for measuring density and viscosity of fluid, the sensor comprising a resonating element arranged to be immersed in the fluid, an actuating/detecting element coupled to the resonating element, and a connector for coupling to the actuating/detecting element. The sensor further comprises a housing defining a chamber isolated from the fluid, the housing comprising an area of reduced thickness defining a membrane separating the chamber from the fluid. The actuating/detecting element is positioned within the chamber so as to be isolated from the fluid and mechanically coupled to the membrane. The resonating element arranged to be immersed in the fluid is mechanically coupled to the membrane. The membrane has a thickness enabling transfer of mechanical vibration between the actuating/detecting element and the resonating element.

The document US 20100154546 describes an apparatus for determining and/or monitoring at least one process variable of a medium. The apparatus includes at least one mechanically oscillatable membrane, which has a plurality of natural eigenmodes; and at least one driving/receiving unit, which excites the membrane to execute mechanical oscillations and/or which receives mechanical oscillations from the membrane. The driving/receiving unit and the membrane are embodied and matched to one another in such a manner, that the membrane executes only mechanical oscillations, which correspond to modes, which lie above the fundamental mode of the membrane. In an embodiment, the driving/receiving unit includes at least one piezoelectric element. The piezoelectric element has at least two separate regions, and the piezoelectric element is arranged and connected with the membrane in such a manner, that the two separate regions of the piezoelectric element excite, each, a section of the membrane to execute mechanical oscillations. If the two regions of the piezoelectric element are supplied either with counter-phase (equal polarization), or with equal phase (opposite polarization), alternating voltage signals, then each region executes a different oscillation, i.e. one region contracts (the thickness decreases) and the other region expands (the thickness increases). This leads to the fact that also the corresponding sections of the membrane, which, in each case, preferably, reside above different regions of the piezoelectric element, also, in each case, execute different oscillations. Thus, in such an apparatus, the two regions of the piezoelectric element supplied with appropriate voltage signals are used to select a desired mode of oscillation of the membrane which itself constitute the resonating element of the apparatus.

Such density and viscosity sensors or apparatuses are well adapted for measurements in harsh environment. However, they are not satisfactory because the vibration modes of the membrane create stationary acoustic waves that interfere with the measurements. This results in measurements accuracy issues.

SUMMARY OF THE INVENTION

It is an object of the invention to propose a density and viscosity sensor and/or measuring method that overcome the above mentioned drawbacks, and in particular cancel, at least greatly reduce interferences due to the stationary acoustic waves created by the membrane.

According to one aspect, there is provided a density and viscosity sensor for measuring density and viscosity of a fluid,
wherein the sensor comprises:
  a housing defining a chamber isolated from the fluid, the housing comprising an area defining a membrane separating the chamber from the fluid;
  a resonating element arranged to be immersed in the fluid and mechanically coupled to the membrane; and
  an actuating/detecting element coupled to the resonating element, the actuating/detecting element being positioned within the chamber and mechanically coupled to the membrane, the actuating/detecting element comprising at least one piezoelectric element comprising two sides substantially parallel to the membrane;
wherein the membrane has a thickness enabling transfer of mechanical vibration between the actuating/detecting element and the resonating element;
wherein:
  one side of the piezoelectric element comprises a single conductive area; and
  another side of the piezoelectric element comprises at least two conductive areas isolated from each other, each conductive area being coupled to an electrical potential of opposite sign relatively to adjacent areas such that the resonating element is driven to vibrate in a selected plane perpendicular to the membrane.

The piezoelectric element may be positioned such that the single conductive area is in contact with the membrane.

The single conductive area may be adhered to the membrane by means of a layer of conductive glue.

The single conductive area may be adhered to the membrane by means of a layer of insulating glue.

Each of the at least two conductive areas may have substantially an identical surface.

The piezoelectric element may comprise four conductive areas isolated from each other such that a pair of conductive areas is adjacent to another pair of conductive areas, each pair of conductive areas being arranged to be coupled to an electrical potential of opposite sign relatively to the respective adjacent pair of conductive areas.

The piezoelectric element may have a cylindrical shape, each of the at least two conductive areas being a thin layer of metallization deposited on a flat surface of the cylindrical shape.

The single conductive area may be arranged to be coupled to an electrical reference or is electrically floating.

The resonating element comprises a beam extending approximately perpendicularly to the membrane, the beam forming a paddle, a bar, or a tuning fork, etc. . . .

The beam may have a transverse axis that is positioned relatively to a longitudinal plane of the at least two conductive areas of the piezoelectric element at an angle of 0°, 45° or 90°.

The density and viscosity sensor may further comprise a temperature sensor positioned within the chamber or outside the chamber.

The density and viscosity sensor may further comprise an electronic arrangement arranged to drive the actuating/detecting element from an actuating mode into a detecting mode and vice-versa.

According to a further aspect, there is provided a logging tool comprising a density and viscosity sensor according to the invention.

According to still a further aspect, there is provided a method for measuring density and viscosity of a fluid comprising the steps of:
  immersion in the fluid of a resonating element of a density and viscosity sensor according to the invention, said sensor comprising a single conductive area on one side of a piezoelectric element, and at least two conductive areas isolated from each other on another side of the piezoelectric element;
  coupling the single conductive area to an electrical potential;
  coupling each of at least two conductive areas to an electrical potential of opposite sign relatively to adjacent areas;
  applying an excitation signal to an actuating/detecting element and detecting a reception signal provided by the actuating/detecting element;
  determining a resonant frequency and quality factor of the resonating element in the fluid; and
  determining density and viscosity of the fluid based on the resonant frequency and the quality factor.

The method and sensor of the invention enable providing reliable and accurate measurements that are not disturbed by stationary acoustic waves created by the membrane.

Further, with the invention uncontrolled potentials that may be transmitted along a pipe or tool to the density and viscosity sensor housing do not affect the measurements. Indeed, in some embodiments the electrical reference may be floating as one side of the piezoelectric element comprises a single conductive area that is isolated from the sensor housing.

Further, the sensor housing, membrane and resonating element may be manufactured as a monolithic entity, resulting in a simple and robust sensor. Thus, the sensor is particularly well adapted for harsh environment applications. It can be manufactured at a reasonable cost compared to prior art density and viscosity sensor used in harsh environment applications.

BRIEF DESCRIPTION OF THE DRAWINGS

Other advantages will become apparent from the hereinafter description of the invention.

The present invention is illustrated by way of examples and not limited to the accompanying drawings, in which like references indicate similar elements.

DETAILED DESCRIPTION

Figure 1:
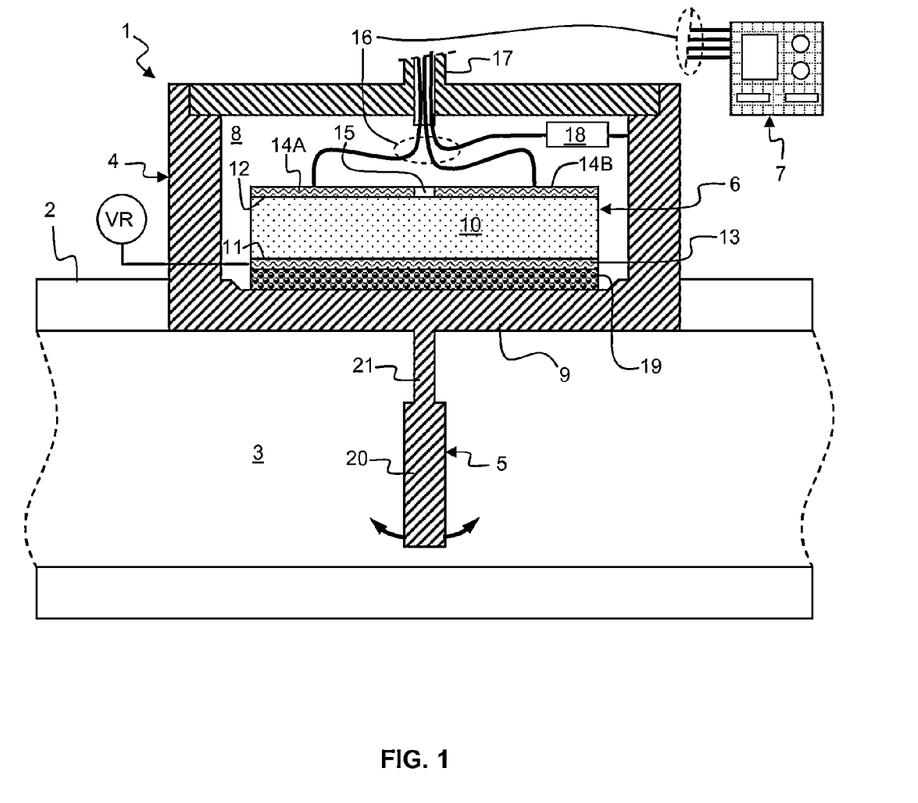
FIG. 1 is a side cross-section view schematically illustrating a density and viscosity sensor of the invention coupled to a pipe.

FIG. 1 is a side cross-section view schematically illustrating a density and viscosity sensor 1 of the invention. The density and viscosity sensor 1 is coupled to a pipe or a container or a tool portion 2 where a fluid 3 flows or is stand still. The coupling relatively to the pipe or the container 2 may be fixed or removable (by means of welding, plugging, screwing, etc. . . . ). The density and viscosity sensor 1 aims at measuring the density and viscosity of said fluid 3.

The density and viscosity sensor 1 may comprise a housing 4, a resonating element 5, an actuating/detecting element 6 and an electronic arrangement 7.

The housing 4 defines a chamber 8 isolated from the fluid 3. The housing comprises an area defining a membrane 9 separating the chamber 8 from the fluid 3.

Figure 9:
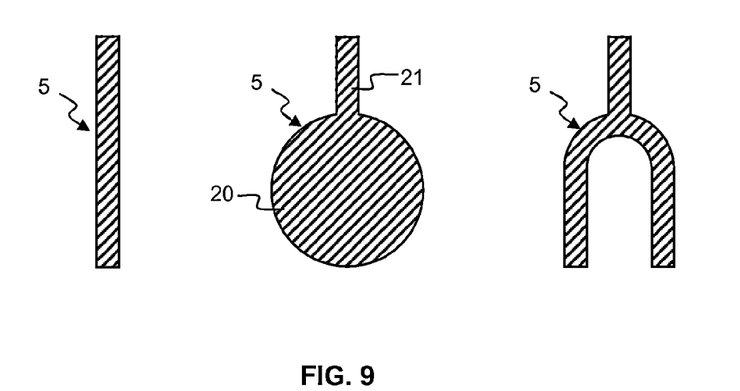
FIG. 9 schematically illustrates in side cross section views various resonating element alternatives.

The resonating element 5 is mechanically coupled to the membrane 9. The resonating element 5 may be immersed in the fluid 3. The resonating element 5 is realized under the form of a beam extending approximately perpendicularly to the membrane 9. The resonating element 5 is mechanically coupled to the membrane 9 substantially at the center thereof. The beam may comprise a first part 20 of rectangular shape and a second part 21 of cylindrical or rectangular shape. Thus, the beam may form approximately a kind of paddle that may be immersed in the fluid 3. The first and second part may be made as a single part or coupled together. The resonating element 5 may be integrally manufactured with the membrane or as a separate part. The rectangular paddle shape is an example as various other kind of resonating element 5 may be alternatively used, for example a bar, a paddle with a first part 20 of circular shape, or a tuning fork as depicted in FIG. 9 left, middle and right, respectively. Other shapes not represented in the drawings may be used, for example a first part of triangular shape, octagonal shape, etc. . . . .

The housing 4, the membrane 9, the resonating element 5 may be manufactured together by machining a single piece of metal. For example, the single piece of metal is a high strength and high corrosion resistance stainless steel like e.g. Inconel. The chamber 8 may be further sealed on its back by means of a metallic connector 17. The metallic connector 17 may be screwed or plug into the housing 4. Additional sealing, e.g. O-ring type sealing (not shown) may be further provided.

The actuating/detecting element 6 is coupled to the resonating element 5. More precisely, the actuating/detecting element 6 is positioned within the chamber 8 and mechanically coupled to the membrane 9. The membrane 9 has a thickness enabling a transfer of the mechanical vibrations between the actuating/detecting element 6 and the resonating element 5. The actuating/detecting element comprises a piezoelectric element or a stack (not shown) of piezoelectric element 10. The piezoelectric element has two sides 11, respectively 12, substantially parallel to the membrane 9.

One side 11 of the piezoelectric element 10 comprises a single conductive area 13. The single conductive area 13 may be coupled to an electrical reference VR, or may be let floating. The piezoelectric element 10 is positioned such that the single conductive area 13 is in mechanical contact with the membrane 9. According to a first alternative, the single conductive area 13 is adhered to the membrane 9 by means of an adhesive layer 19 of conductive glue (conductive balls may be embedded in the adhesive layer 19). In this case, the single conductive area 13 is at the electrical reference VR by means of the metallic housing 4 and membrane 9. The metallic housing 4 and membrane 9 may be formed in a unique piece of metal, or as separate piece of metal welded together. According to a second alternative, the single conductive area 13 is adhered to the membrane 9 by means of an adhesive layer 19 of insulating glue. In this case, the single conductive area 13 is left at a floating potential. This enables getting rid of uncontrolled potentials that may be transmitted along the pipe, or container, or tool 2 to the density and viscosity sensor housing 4. Typically, in the frame of oilfield industry, a logging tool may comprise various elements like motors, pads, etc. . . . electrically coupled together because they are mostly made of stainless steel material. Some of these elements may require hundred Volt of power for operation and generates uncontrolled potentials that may be transmitted along the tool.

Another side 12 of the piezoelectric element comprises at least two conductive areas 14A, 14B separated from each other by an electrical insulator 15. Practically, the electrical insulator 15 may be an air gap obtained by abrasion of the metalized layer or by a controlled sputtering of metallization material onto the ceramic. Each conductive area 14A, 14B is arranged to be coupled to an opposite potential, i.e. an electrical potential V1 or V2 of opposite sign relatively to the adjacent area 14B, 14A. More precisely, with respect to the embodiment illustrated in FIGS. 1 and 2, the first conductive areas 14A may be coupled to an electrical potential V1, while the second conductive areas 14B that is adjacent to the first conductive areas 14A may be coupled to an opposite electrical potential V2, and vice-versa, both electrical potential being for example a sinusoidal signal (in phase opposition). These conductive areas 14A, 14B and their respective polarizations form a first embodiment of a compensation arrangement used to compensate for stationary acoustic waves induced when the resonating element together with the membrane are vibrating during the measurements. The operation of the compensation arrangement will be explained in details hereinafter.

A temperature sensor 18, e.g. a thermistance, a diode, etc. . . . may be positioned within the chamber 8 or outside the chamber 8 while close to the density and viscosity sensor. The temperature effects on density and viscosity measurements may be corrected by means of the temperature measurements.

The electronic arrangement 7 may comprise various entities, for example a powering unit, a processor, an oscillator, an amplifier, various switch, a memory, a communication interface. The electronic arrangement 7 is arranged to drive the actuating/detecting element 6 from an actuating mode into a detecting mode and vice-versa. The electronic arrangement 7 may be coupled to the conductive areas 14A, 14B, to the single conductive area 13 and to the temperature sensor 18 by means of various electrical cables 16. The electrical cables may be integrated in the connector 17. The electronic arrangement 7 may provide the electrical reference VR, and the electrical potentials V1 and V2. Though, the electronic arrangement 7 is depicted as located outside the chamber 8, it may alternatively be located inside the chamber 8.

Figure 10:
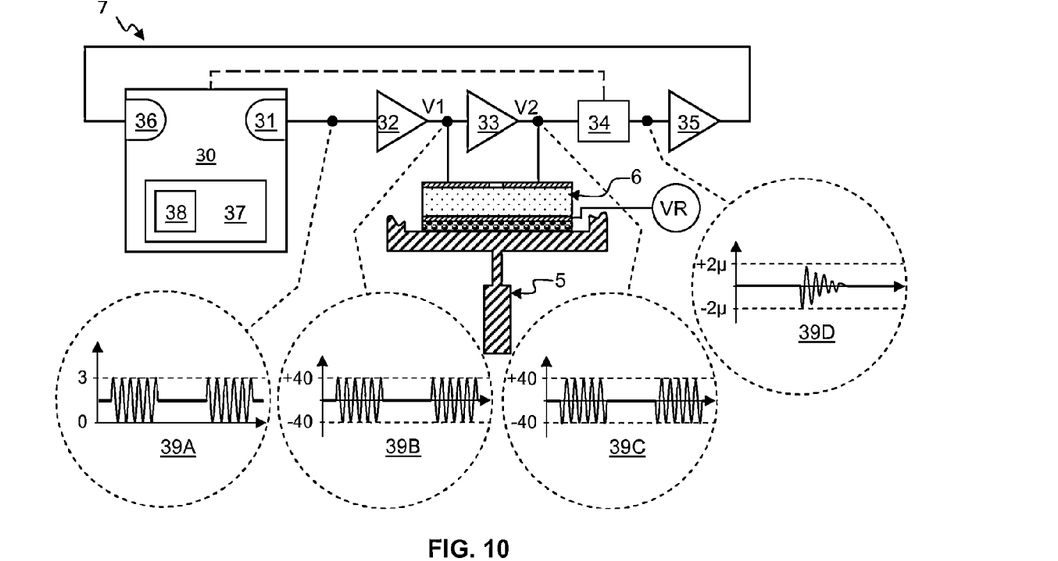
FIG. 10 schematically illustrates an example of electronic arrangement to operate the density and viscosity sensor.

FIG. 10 schematically illustrates an example of such an electronic arrangement 7 used to operate the density and viscosity sensor 1. The electronic arrangement 7 comprises a processing entity 30, an amplifier 32, an inverter 33, a switch 34 and another amplifier 35. The processing entity 30 comprises a digital to analog output 31 providing an excitation signal 39 that is amplified by the amplifier 32. The excitation signal 39A provided by the processing entity 30 may be in the range of 1 to 3 Volt. The amplified excitation signal 39B provided by the amplifier 32 may be in the range of 5 to 40 Volt depending on the energy to be transmitted to the membrane and the resonating element. The amplifier 32 applies the amplified excitation signal V1 (39B) to one of the conductive area of the actuating/detecting element 6 and to the inverter 33. The inverter 33 provides an opposite excitation signal V2 (39C) to one of the adjacent conductive area of the actuating/detecting element 6. Once a vibration has been established by exciting the piezoelectric element and after a defined relaxation duration, a reception signal 39D representative of the vibration of the resonating element in the fluid is measured. The switch 34 is closed by the processing entity 30 and the reception signal 39D representative of strain variation of the membrane mechanically coupled to the resonating element is amplified by the other amplifier 35 (the reception signal 39D is typically in the micro-Ampere order). The output of the other amplifier 35 is connected to an analog to digital input 36 of the processing entity 30. The processing entity 30 comprises a memory 37 and may execute a software 38. Based on the reception signal (a series of measurements may be required), the processing entity 30 determines a resonant frequency and quality factor of the resonating element in the fluid. Subsequently, the processing entity 30 infers the density and viscosity of the fluid based on the resonant frequency and the quality factor.

Figure 2:
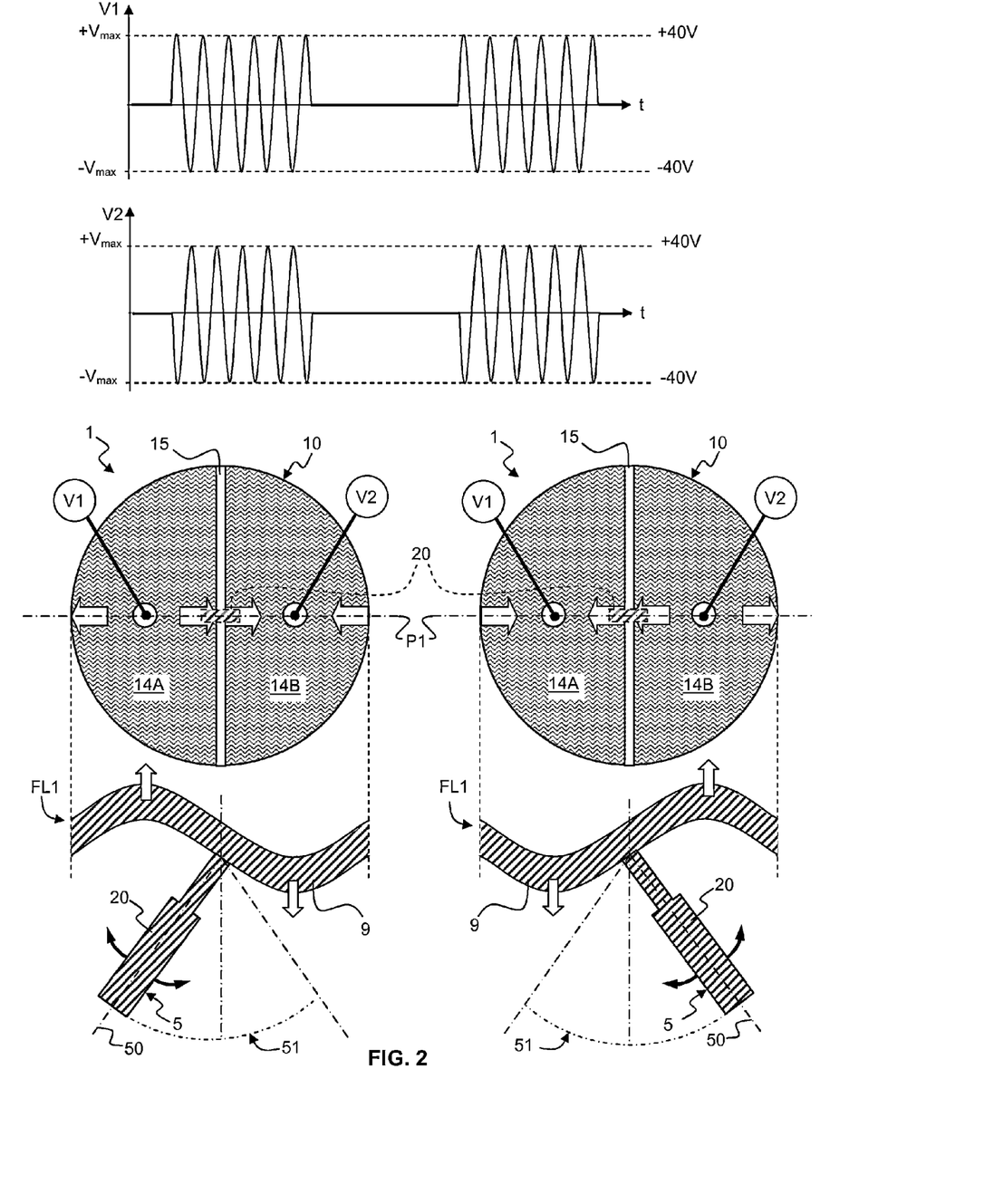
FIG. 2 is a top view (middle part) of a piezoelectric element of a density and viscosity sensor of a first embodiment and a side cross-section view (bottom part) of the corresponding flexion of the piezoelectric element and the membrane schematically illustrating the principle of operation of the invention when a sinusoidal excitation signal (top part) is applied.

FIG. 2 is a top view schematically illustrating a first embodiment of a piezoelectric element 10 of the density and viscosity sensor of the invention.

The piezoelectric element 10 comprises two conductive areas 14A, 14B separated from each other by the electrical insulator 15.

The piezoelectric element 10 has a cylindrical shape. Each conductive area has the shape of a half circle. Thus, the conductive areas have substantially an identical surface. Each conductive area is a thin layer of metallization (e.g. Ni, Cr, Ag) deposited on the flat surface of the cylindrical shape. The conductive areas form adjacent conductive areas that are separated by the electrical insulator 15 having the shape of a line. The first conductive area 14A may be coupled to an electrical potential V1 while the second conductive area 14B may be coupled to an opposite electrical potential V2. Both electrical potential may be for example a sinusoidal excitation signal as depicted in the top part of FIG. 2. As an example, the sinusoidal amplified excitation signal applied to the conductive areas varies between a voltage $+V_{max}$ around +40 V and and voltage $-V_{max}$ around −40 V.

The bottom part of FIG. 2 shows a side cross-section view of the corresponding flexion FL1 of the piezoelectric element and the membrane when such a sinusoidal excitation signal is applied to the piezoelectric element. This schematically illustrating the principle of compensation of the invention.

When a piezoelectric element is submitted to an electrical potential, the piezoelectric element is put in compression or in extension depending on the polarity of said potential. As the piezoelectric element is mechanically coupled to the membrane, the compression or extension of the piezoelectric element is transformed in a flexion of the membrane towards the fluid or towards the chamber. The flexion of the membrane results in moving a quantity of fluid close to the membrane. When an oscillating excitation signal is applied to the piezoelectric element, this results in creating an acoustic wave propagating in the fluid. According to the present invention, one side 11 of the piezoelectric element 10 being coupled to a defined potential while the other side 12 comprises two conductive area 14A, 14B being coupled to opposite potential V1, respectively V2, the portion of piezoelectric element facing the first conductive area 14A is in extension while the portion of piezoelectric element facing the second conductive area 14B is in compression. This results in the part of the membrane 9 facing the first conductive area 14A bending towards the chamber 8, while the part of the membrane 9 facing the second conductive area 14B bending towards the fluid 3. When the portions of piezoelectric element are submitted to excitation signals of the sinusoidal type of opposite polarities as depicted in the top part of FIG. 2, the hereinbefore described flexions of the respective membrane part alternate. As a consequence, the balance of fluid movement is substantially nil because the volume of fluid displaced resulting of the flexion of the membrane 9 towards the chamber 8 is compensated by the volume of fluid displaced resulting of the flexion of the membrane 9 towards the fluid 3. Further, as a result of the application of the excitation signals of the sinusoidal type of opposite polarities, the resonating element 5 of longitudinal axis 50 substantially perpendicular to the membrane 9 vibrates in an angular sector 51 in the longitudinal plane P1. The resonating element 5 vibrates in its plane without the membrane generating any parasitic acoustic wave. As a consequence, there is not any parasitic resonance generated by said parasitic acoustic wave in a frequency range of measurements. Thus, the measurements related to the density and viscosity properties of the fluid are not affected by any parasitic signal.

Figure 3:
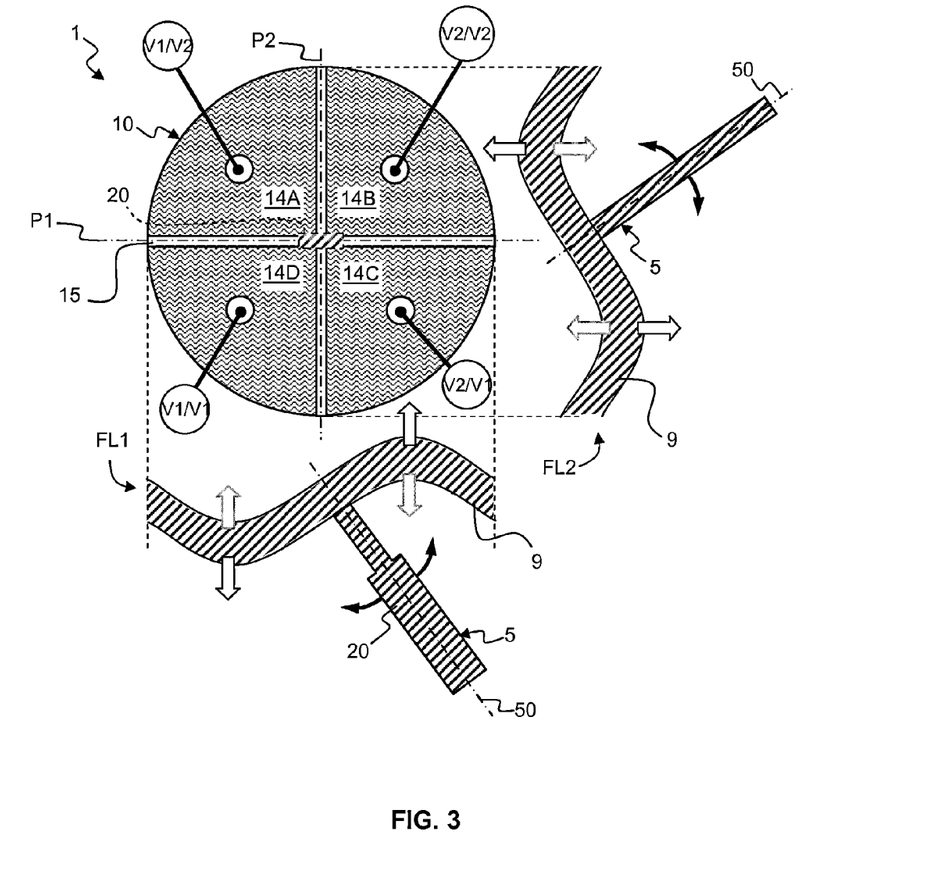
FIG. 3 is a top view schematically illustrating a second embodiment of a piezoelectric element of a density and viscosity sensor of the invention and the corresponding flexion of the piezoelectric element and the membrane.

FIG. 3 is a top view schematically illustrating a second embodiment of a piezoelectric element 10 of a density and viscosity sensor of the invention.

The piezoelectric element 10 comprises four conductive areas 14A, 14B, 14C, 14D separated from each other by the electrical insulator 15.

The piezoelectric element 10 has a cylindrical shape. Each conductive area 14A, 14B, 14C and 14D has the shape of a quadrant. Thus, the conductive areas have substantially an identical surface. Each conductive area 14A, 14B, 14C, 14D is a thin layer of metallization (e.g. Ni, Cr, Ag) deposited on the flat surface of the cylindrical shape. The conductive areas form adjacent conductive areas that are separated by the electrical insulator 15 having the shape of a cross. These conductive areas 14A, 14B, 14C, 14D and their respective polarizations form a second embodiment that enables:

compensating for the stationary acoustic waves induced when the resonating element together with the membrane are vibrating during the measurements as explained hereinbefore with respect to the first embodiment; and selecting the mode of resonance of the resonating element 5 in either the longitudinal plane P1 or the transverse plane P2.

In a first mode of operation, the first conductive area 14A and the fourth conductive area 14D may be coupled to an electrical potential V1, while the second conductive area 14B and the third conductive area 14C may be coupled to an opposite electrical potential V2. Both electrical potential may be for example a sinusoidal signal as depicted in FIG. 2. The bottom part of FIG. 3 shows a side cross-section view of the corresponding flexion FL1 of the piezoelectric element and the membrane when a sinusoidal excitation signal is applied to the piezoelectric element. In this case, the resonating element 5 of longitudinal axis 50 substantially perpendicular to the membrane 9 is driven to vibrate in the longitudinal plane P1. The resonating element 5 vibrates in its plane without the membrane generating any parasitic acoustic wave. In this mode, the resonating element 5 vibrates in the fluid 3 and drags through the fluid in shear. This vibration is dependent upon the resistance to shear of the fluid, and thus the corresponding measurements are related to the fluid viscosity.

In a second mode of operation, the first conductive area 14A and the second conductive area 14B may be coupled to an electrical potential V2, while the third conductive area 14C and the fourth conductive area 14D may be coupled to an opposite electrical potential V1. Both electrical potential may be for example a sinusoidal signal as depicted in FIG. 2. The right part of FIG. 3 shows a side cross-section view of the corresponding flexion FL2 of the piezoelectric element and the membrane when a sinusoidal excitation signal is applied to the piezoelectric element. In this case, the resonating element 5 of longitudinal axis 50 substantially perpendicular to the membrane 9 is driven to vibrate in the transverse plane P2. The resonating element 5 vibrates in its plane without the membrane generating any parasitic acoustic wave. In this mode, the resonating element 5 vibrates in the fluid 3 and displaces some of the surrounding fluid. The effective mass of the resonating element 5 is increased by an amount of mass determined by the volume of fluid entrained by the first part 20, and thus the corresponding measurements are related to the fluid density.

Figure 4:
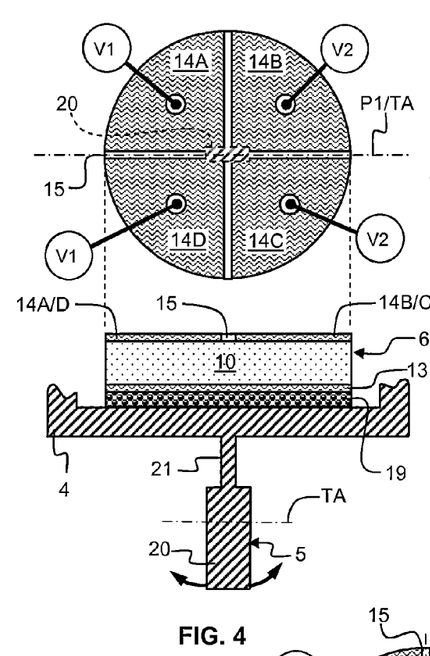
FIGS. 4, 5 and 6 show top views (top part) and partial side cross-section views (bottom part) schematically illustrating various angular position of the beam relatively to the piezoelectric element according to the first and second embodiment of the invention.
Figure 5:
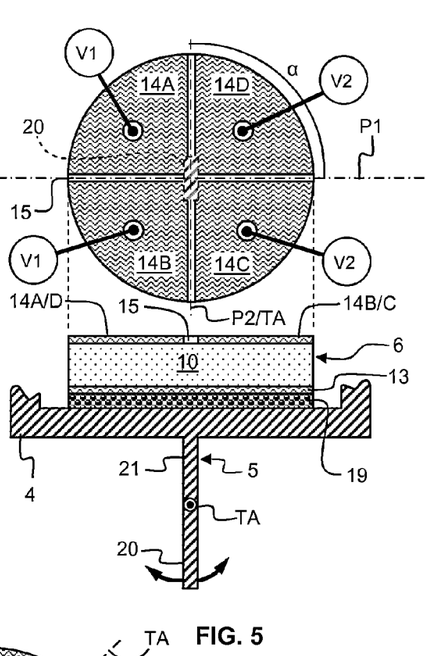
Figure 6:
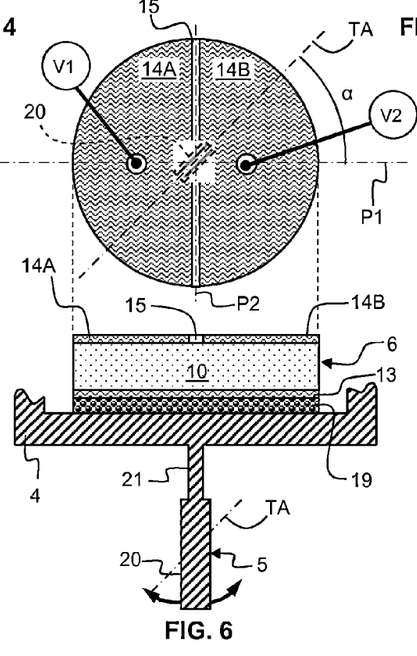

FIGS. 4, 5 and 6 show top views (top part) and partial side cross-section views (bottom part) schematically illustrating various angular position of the first part of the beam 20 relatively to the piezoelectric element 10 according to the first (FIG. 6) and second (FIGS. 4 and 5) embodiment of the invention. The first part of the beam 20 has a rectangular cross-section extending longitudinally approximately perpendicularly to the membrane 9. A transverse axis TA of the first part of the beam 20 is defined as an axis parallel to the membrane 9 surface. The orientation of the first part of the beam enables selecting a particular mode of resonance, or a combination of modes of resonance that is preferred for a particular application of the density and viscosity sensor.

In FIG. 4, the orientation of the first part of the beam 20 is such that the transverse axis TA forms relatively to the longitudinal plane P1 an angle α of 0°. In this case, the first part of the beam 20 is driven to vibrate in the longitudinal plane P1. In this mode, the first part of the beam 20 vibrates in the fluid and drags through the fluid in shear. This vibration is dependent upon the resistance to shear of the fluid, and thus the corresponding measurements are related to the fluid viscosity.

In FIG. 5, the orientation of the beam 20 is such that the transverse axis TA forms relatively to the longitudinal plane P1 of the four conductive areas 14A, 14B, 14C, 14D of the piezoelectric element 10 an angle α of 90°. In this case, the first part of the beam 20 is driven to vibrate in the transverse plane P2 perpendicular to the longitudinal plane P1. In this mode, the first part of the beam 20 vibrates in the fluid 3 and displaces some of the surrounding fluid. The effective mass of the first part of the beam 20 is increased by an amount of mass determined by the volume of fluid entrained by said first part, and thus the corresponding measurements are related to the fluid density.

In FIG. 6, the orientation of the beam 20 is such that the transverse axis TA forms relatively to the longitudinal plane P1 of the two conductive areas 14A, 14B of the piezoelectric element 10 an angle α of 45°. In this case, the first part of the beam 20 is driven to vibrate in the longitudinal plane P1. In this combined mode, the corresponding measurements are related both to the fluid viscosity and density at the same time.

Alternatively, other value of the angle α may be possible (not shown).

Figure 7:
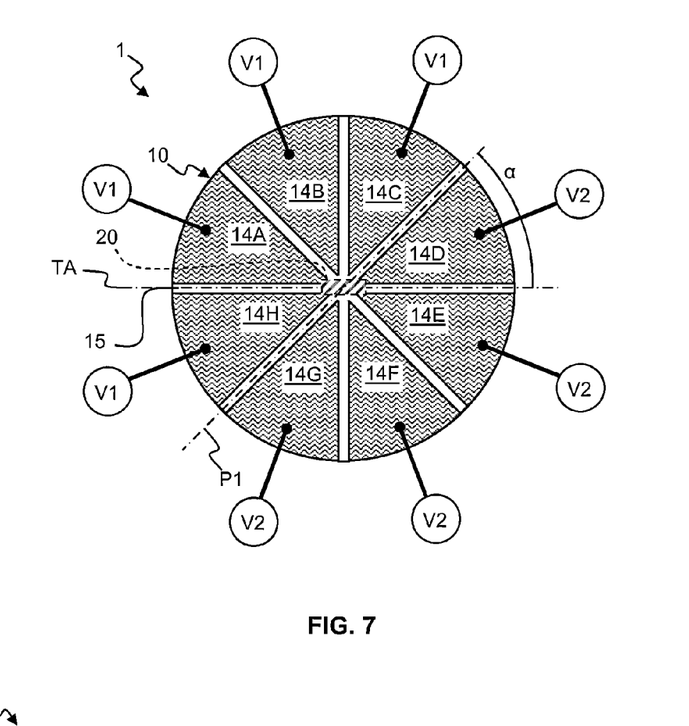
FIGS. 7 and 8 are top views schematically illustrating a third and fourth embodiment of a piezoelectric element of a density and viscosity sensor of the invention, respectively.

FIG. 7 is a top view schematically illustrating a third embodiment of a piezoelectric element of a density and viscosity sensor of the invention. This embodiment differs from the first and second embodiment in that the piezoelectric element 10 is provided with eight conductive areas 14A, 14B, 14C, 14D, 14E, 14F, 14G, and 14H. Each conductive areas 14A, 14B, 14C, 14D, 14E, 14F, 14G, and 14H may be coupled to an electrical potential V1 or V2 (sinusoidal excitation signal as hereinbefore described in relation with FIG. 2). A plurality of conductive areas, for example 14A, 14B, 14C and 14H may be grouped together to form a first zone submitted to the electrical potential V1. Another plurality of conductive areas, for example 14D, 14E, 14F and 14G may be grouped together to form a second zone submitted to the opposite electrical potential V2. In this manner, it is possible to define and precisely select the longitudinal plane P1 and thus to control the vibration of the first part of the beam according to the angle α for a defined position of the first part of the beam 20 relatively to the conductive areas. This enables selecting a particular mode of resonance, or a combination of modes of resonance that is preferred for a particular application of the density and viscosity sensor.

It should be appreciated that, though the embodiment described and depicted embodiments comprising two (FIG. 2), four (FIG. 3), and eight (FIG. 7) conductive areas on the piezoelectric element, other embodiments may be imagined that comprises more conductive areas.

Figure 8:
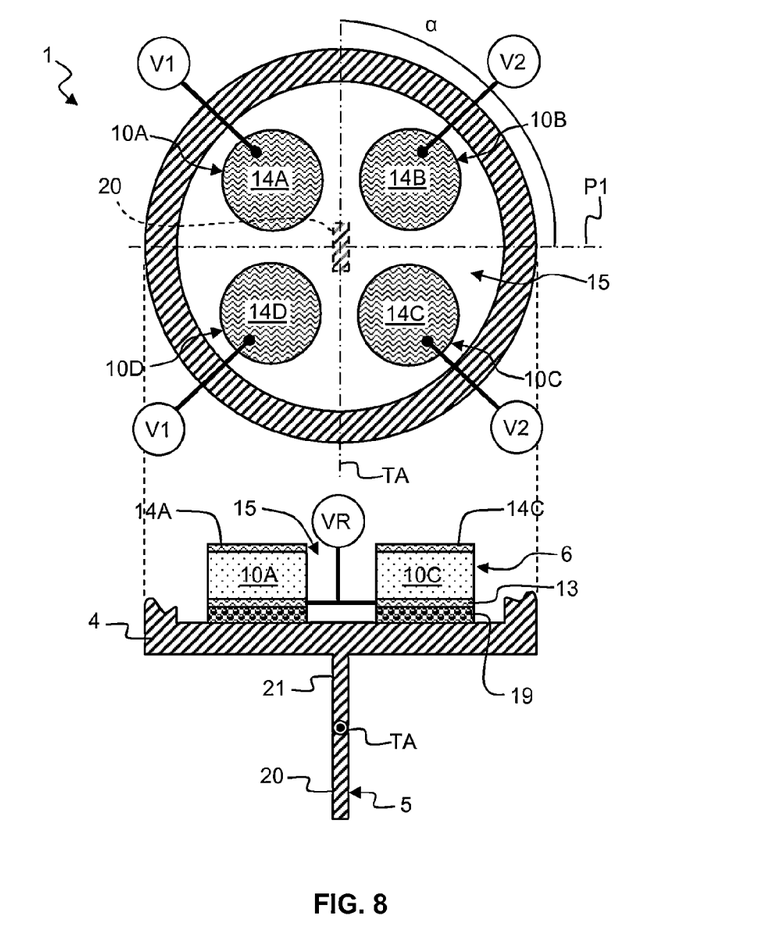

FIG. 8 is a top view schematically illustrating a fourth embodiment of a piezoelectric element of a density and viscosity sensor of the invention. This embodiment differs from the other embodiments in that multiple independent piezoelectric elements, for example four piezoelectric elements 10A, 10B, 10C and 10D instead of a single piezoelectric element 10 are provided. According to this embodiment, one side of each the independent piezoelectric elements is coupled to the same potential VR, while the other side of each the independent piezoelectric elements is arranged to be coupled to the appropriate electrical potential V1 or V2. The operation of the density and viscosity sensor is similar to the other embodiments. The example of four independent piezoelectric elements is not limitative, as this value may be changed to for example two, six, eight, etc. . . . independent piezoelectric elements as desired for a particular measurement application.

Figure 11:
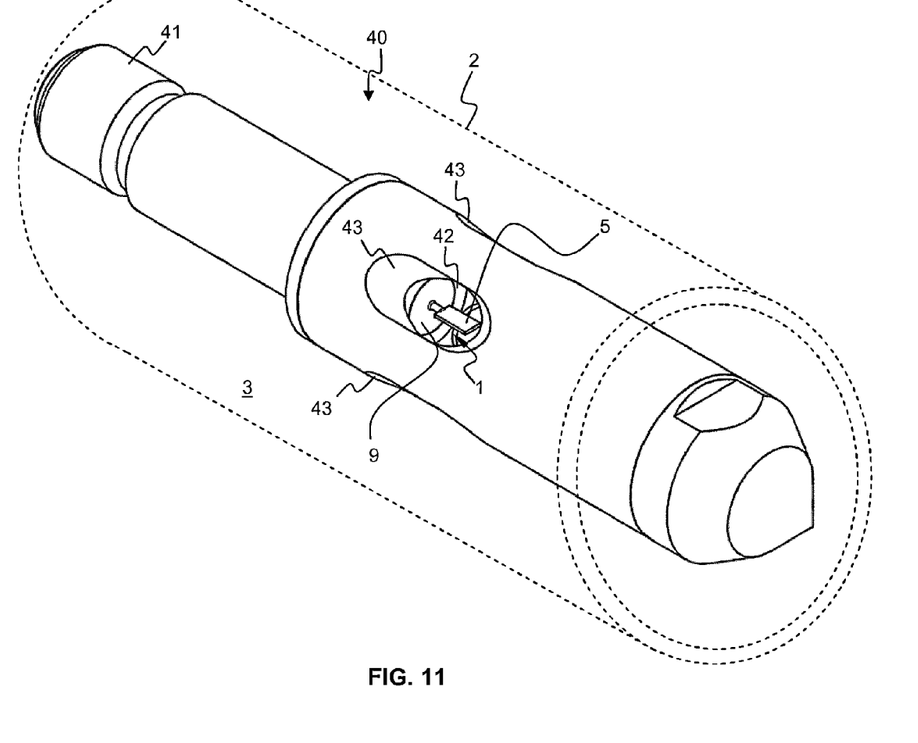
FIG. 11 schematically illustrates an example of application of the density and viscosity sensor of the invention.

FIG. 11 schematically illustrates an example of the density and viscosity sensor 1 in the oilfield exploration domain of application. The density and viscosity sensor 1 is fitted within a tool head 40 that may be moved within a casing 2 filled with hydrocarbon based fluid 3. The tool head 40 comprises a connector 41 for further coupling with a tool body of a logging tool (not shown), and a chamber 42 communicating with the surrounding fluid 3 through a plurality of holes 43. The density and viscosity sensor 1 is secured within the tool head 40 in such a manner that the membrane 9 and the resonating element 5 are contacting said fluid 3. Thus, the density and/or viscosity of said fluid can be measured at different place (depth) of the casing and at various times so as to measure for example the evolution of the density and viscosity of the hydrocarbon fluid produced by a well. The density and viscosity sensor of the present disclosure may be applied in various other industries, for example the chemical industry, the food industry, the aerospace industry, etc. . . . .

The drawings and their description hereinbefore illustrate rather than limit the invention.

Although a drawing shows different functional entities as different blocks, this by no means excludes implementations in which a single entity carries out several functions, or in which several entities carry out a single function. In this respect, the drawings are very diagrammatic. The functions of the various elements shown in the FIGS., including any functional blocks, may be provided through the use of dedicated hardware as well as hardware capable of executing software in association with an appropriate software. When provided by a processor, the functions may be provided by a single dedicated processor, by a single shared processor, or by a plurality of individual processors, some of which may be shared. Moreover, explicit use of the term "entity" should not be construed to refer exclusively to hardware capable of executing software, and may implicitly include, without limitation, digital signal processor (DSP) hardware, processor, application specific integrated circuit (ASIC), field programmable gate array (FPGA), read only memory (ROM) for storing software, random access memory (RAM), and non volatile storage. Other hardware, conventional and/or custom, may also be included.

It should be appreciated by those skilled in the art that any block diagrams herein represent conceptual views of illustrative elements embodying the principles of the invention. Further, the various elements forming the sensor as depicted are very schematic and not necessary full scale relatively to each other. As an example, the membrane 9 may have a thickness of approximately 0.5 mm, the piezoelectric element 10 may have a thickness of approximately 0.25 mm, and the housing 4 may have a thickness of approximately 4 mm.

It should be appreciated by those skilled in the art that coupling the adjacent conductive areas to electrical potentials of opposite signs is only an example, the same effect can be achieved with alternating signals of equal polarization but in counter-phase.

Any reference sign in a claim should not be construed as limiting the claim. The word "comprising" does not exclude the presence of other elements than those listed in a claim. The word "a" or "an" preceding an element does not exclude the presence of a plurality of such element.

The invention claimed is:

1. A density and viscosity sensor for measuring density and viscosity of a fluid,
wherein the sensor comprises:
a housing defining a chamber isolated from the fluid, the housing comprising an area defining a membrane separating the chamber from the fluid;
a resonating element arranged to be immersed in the fluid and mechanically coupled to the membrane; and
an actuating/detecting element coupled to the resonating element, the actuating/detecting element being positioned within the chamber and mechanically coupled to the membrane, the actuating/detecting element comprising at least one piezoelectric element comprising two sides substantially parallel to the membrane;
wherein the membrane has a thickness enabling transfer of mechanical vibration between the actuating/detecting element and the resonating element;
and wherein:
one side of the piezoelectric element comprises a single conductive area; and
another side of the piezoelectric element comprises at least two conductive areas isolated from each other, each conductive area being coupled to an electrical potential of opposite sign relatively to adjacent areas such that the resonating element is driven to vibrate in a selected plane perpendicular to the membrane.

2. The density and viscosity sensor of claim 1, wherein the piezoelectric element is positioned such that the single conductive area is mechanically connected with the membrane.

3. The density and viscosity sensor of claim 2, wherein the single conductive area is adhered to the membrane by means of a layer of insulating glue thereby coupling the single conductive area to a floating potential.

4. The density and viscosity sensor of claim 1, wherein the at least two conductive areas have substantially an identical surface.

5. The density and viscosity sensor of claim 1, wherein the piezoelectric element comprises four conductive areas isolated from each other such that a pair of conductive areas is adjacent to another pair of conductive areas, each pair of conductive areas being arranged to be coupled to an electrical potential of opposite sign relative to the respective adjacent pair of conductive areas.

6. The density and viscosity sensor of claim 1, wherein the piezoelectric element has a cylindrical shape, each of the at least two conductive areas being a thin layer of metallization deposited on a flat surface of the cylindrical shape.

7. The density and viscosity sensor of claim 1, wherein the resonating element comprises a beam extending approximately perpendicularly to the membrane.

8. The density and viscosity sensor of claim 7, wherein the beam has a transverse axis that is positioned relative to a longitudinal plane of the at least two conductive areas of the piezoelectric element at an angle that is a multiple of 45° selected from the group consisting of the elements of 0°, 45°, and 90°.

9. The density and viscosity sensor of claim 7, wherein the beam is a bar.

10. The density and viscosity sensor of claim 1, wherein the sensor further comprises a temperature sensor positioned within the chamber.

11. The density and viscosity sensor of claim 1, wherein the sensor further comprises an electronic arrangement arranged to drive the actuating/detecting element from an actuating mode into a detecting mode and vice-versa.

12. A logging tool comprising a density and viscosity sensor for measuring density and viscosity of a fluid,
wherein the sensor comprises:
a housing defining a chamber isolated from the fluid, the housing comprising an area defining a membrane separating the chamber from the fluid;
a resonating element arranged to be immersed in the fluid and mechanically coupled to the membrane; and
an actuating/detecting element coupled to the resonating element, the actuating/detecting element being positioned within the chamber and mechanically coupled to the membrane, the actuating/detecting element comprising at least one piezoelectric element comprising two sides substantially parallel to the membrane;
wherein the membrane has a thickness enabling transfer of mechanical vibration between the actuating/detecting element and the resonating element;
and wherein:
one side of the piezoelectric element comprises a single conductive area; and
another side of the piezoelectric element comprises at least two conductive areas isolated from each other, each conductive area being coupled to an electrical potential of opposite sign relative to adjacent areas such that the resonating element is driven to vibrate in a selected plane perpendicular to the membrane.

13. The logging tool of claim 12, wherein the piezoelectric element is positioned such that the single conductive area is mechanically connected with the membrane.

14. The logging tool of claim 12, wherein the single conductive area is adhered to the membrane by means of a layer of conductive glue thereby coupling the single conductive area to an electrical reference.

15. The logging tool of claim 12, wherein the at least two conductive areas have substantially an identical surface.

16. The logging tool of claim 12, wherein the piezoelectric element comprises four conductive areas isolated from each other such that a pair of conductive areas is adjacent to another pair of conductive areas, each pair of conductive areas being arranged to be coupled to an electrical potential of opposite sign relative to the respective adjacent pair of conductive areas.

17. The logging tool of claim 12, wherein the piezoelectric element has a cylindrical shape, each of the at least two conductive areas being a thin layer of metallization deposited on a flat surface of the cylindrical shape.

18. The logging tool of claim 12, wherein the resonating element comprises a beam extending approximately perpendicularly to the membrane.

19. The logging tool of claim 18, wherein the beam has a transverse axis that is positioned relative to a longitudinal plane of the at least two conductive areas of the piezoelectric element at an angle that is a multiple of 45° selected from the group consisting of the elements of 0°, 45°, and 90°.

20. The logging tool of claim 18, wherein the beam is a bar.

21. The logging tool of claim 12, wherein the sensor further comprises a temperature sensor positioned within the chamber.

22. The logging tool of claim 12, wherein the sensor further comprises an electronic arrangement arranged to drive the actuating/detecting element from an actuating mode into a detecting mode and vice-versa.

23. A method for measuring density and viscosity of a fluid comprising the steps of:
- immersion in the fluid of a resonating element of a density and viscosity sensor, said sensor comprising a single conductive area on one side of a piezoelectric element, and at least two conductive areas isolated from each other on another side of the piezoelectric element;
- coupling the single conductive area to an electrical potential;
- coupling each of at least two conductive areas to an electrical potential of opposite sign relative to adjacent areas;
- applying an excitation signal to an actuating/detecting element and detecting a reception signal provided by the actuating/detecting element;
- determining a resonant frequency and quality factor of the resonating element in the fluid; and
- determining density and viscosity of the fluid based on the resonant frequency and the quality factor.

* * * * *